United States Patent [19]
Rabjohns et al.

[11] Patent Number: 5,349,199
[45] Date of Patent: Sep. 20, 1994

[54] SENSING APPARATUS FOR REDUCING SHEET DETECTION AND REGISTRATION ERRORS BY USING MULTIPLE LIGHT BEAM REFLECTIONS

[75] Inventors: Douglas T. Rabjohns; Gary W. Roscoe, both of Fairport, N.Y.

[73] Assignee: Xerox Corporation, Stamford, Conn.

[21] Appl. No.: 53,745

[22] Filed: Apr. 29, 1993

[51] Int. Cl.⁵ .............................. G01N 21/86
[52] U.S. Cl. ....................... 250/561; 250/222.1
[58] Field of Search ............... 250/561, 571, 222.1, 250/223 R; 356/375, 384, 385, 386

[56] References Cited

U.S. PATENT DOCUMENTS

| Patent No. | Date | Inventor | Class |
|---|---|---|---|
| 4,743,775 | 5/1988 | Edgar | 250/571 |
| 4,793,605 | 12/1988 | Tajima | 271/9 |
| 4,805,893 | 2/1989 | Kusaka | 271/258 |
| 4,885,461 | 12/1989 | Mattila et al. | 250/223 B |
| 4,924,106 | 5/1990 | Tolmie, Jr. | 250/561 |
| 5,019,249 | 5/1991 | Sugai et al. | 209/534 |
| 5,075,543 | 12/1991 | Courtney | 250/223 R |
| 5,235,192 | 8/1993 | Chase et al. | 250/571 |

OTHER PUBLICATIONS

Anderson et al., "Transmissive Document Sensor", IBM Technical Disclosure Bulletin, vol. 22, No. 4, Sep. 1979.

Amarakoon, "Optical Sensor", Xerox Disclosure Journal, vol. 10, No. 5, Oct. 1985.

*Primary Examiner*—David C. Nelms
*Assistant Examiner*—K. Shami

[57] ABSTRACT

An apparatus for sensing the presence or an edge of a sheet, including a light emitter, a set of reflectors and at least one light detecting member. A light beam is reflected between the emitter and detector in a repeating wave form so as to intersect a sheet path; interruption of the light beam indicates the presence of a sheet. False indications of the presence, absence or true edge of the sheet such as may be caused by sheet holes or edge irregularities are avoided by the multiple passes of a beam of light across the path of the sheet. A continuous cleaning action of the sensor may be provided by the movement of the sheet over the light emitters, light detectors and/or reflectors. The sheet sensors are useful in detecting and/or correcting sheet skew, misregistration and other potential sheet handling problems. Through the use of optic fibers, wires or other means, the light emitter(s) and light detectors that may service a network of sheet sensors positioned throughout a copying or printing machine which may be centralized and otherwise assembled in efficient modularized configurations.

14 Claims, 6 Drawing Sheets

SENSING APPARATUS FOR REDUCING SHEET DETECTION AND REGISTRATION ERRORS BY USING MULTIPLE LIGHT BEAM REFLECTIONS

This invention relates generally to sheet handling devices, and more particularly concerns an apparatus and method for correctly sensing the leading edge, the trailing edge and/or presence of a sheet so as to avoid sheet handling errors that might otherwise occur as a result of pre-drilled sheet holes, tears and other variances in a sheet surface, or that might occur as a result of sheet skew, misalignment, misregistration, paper jams or other sheet handling situations.

Xerographic reproduction and printing machines utilize sheet handling devices which often incorporate a number of sensors to monitor sheet presence, edge location, dimensions, alignment, registration, jamming and other conditions relating to sheets passing through such machines. Extensive arrays of such sensors are being incorporated into technologically advanced machines to increase their capabilities and reliability, and to prevent hazardous conditions and/or damage to machines that may be caused by sheet jamming or other problems. Perhaps most notably, sheet sensors can eliminate numerous preparation and instruction input tasks formerly required of operators. The employment of compact and reliable single and multi-function sensors that can be used more than one location in machine can further the capabilities of such machines, while offering important manufacturing and repair cost advantages and cost savings.

Sheet presence, alignment and edge detection systems have heretofore existed which make use of light emitters and receptors. An important drawback to many such sensors is their inability to correctly "ignore" sheet holes, folded corners or other surface and edge irregularities so as to eliminate sheet and edge sensing false alarms. Elaborate computer programs have been developed to utilize "spot" sensors, which may employ one or two light beams in close proximity to each other generally positioned at a corner of a passing sheet, as well as other sensor configurations that are only able to provide information from a small cross sectional area. In many situations (such as edge detection in predrilled paper sheets), such programs must use such corner/spot sensors to "predict" (rather than know) where the lead edge and/or trail edge of a sheet may lie For example, when a spot or corner sensor is first triggered by the lead edge of a sheet, the program may be set so as to permit at least 8 inches of an 8½ inch sheet (moving at a constant or variable velocity) to pass by the spot sensor before the program will use the spot sensor to "look" for the trail edge of the sheet. Even so, when predrilled or otherwise nonstandard sheets (size, hole placement, etc.) are run through the machine, the spot sensor (which may be able to ignore standard size holes in the usual places) may mistake a nonstandard hole near an edge as the edge itself, disrupting the timing, registration, or other essential processes being carried out by the machine. As such, when spot sensors are used to control drive motors or to monitor sheet timing, directing, registration and/or aligning mechanisms, their use can become quite problematic.

Due to these and other drawbacks, known spot and corner sensors generally inhibit the ability of automated machines and systems to correctly deal with difficult or unusual situations which may not have been anticipated by their designers. Whether the situation involves non-standard sheet holes, edges or dimensions, or sheet skew, a machine using spot sensors may be unable to adequately recognize and deal with the situation. Although it is known to utilize an array of spot sensors, such an array must be carefully arranged and tuned so as to cooperatively sense the desired condition. Such arrays of spot sensors may add complexity, expense, power consumption, undesirable heat, failure points and otherwise undesirably degrade the reliability and capability of the machine.

Various sensors have been devised for sensing the corners, edges and/or presence of sheets, including the following disclosures which appear to be relevant:

U.S. Pat. No. 5,019,249 Patentee: Sugai et al. Issued: May 28, 1991

U.S. Pat. No. 5,075,543 Patentee: Courtney Issued: Dec. 24, 1991

U.S. Pat. No. 4,793,605 Patentee: Tajima Issued: Dec. 27, 1988

U.S. Pat. No. 4,805,893 Patentee: Kusaka Issued: Feb. 21, 1989

IBM Technical Disclosure Bulletin T. H. Anderson, R. F. Harding and R. J. Keller Vol. 22, No. 4, pp. 1585–1586, September 1979

Xerox Disclosure Journal K. B. Amarakoon Vol. 10, No. 5, p. 311, September/October 1985

U.S. Pat. No. 5,019,249 discloses a sheet handler which includes a plurality of sensors for detecting the existence of the sheets of paper as they are transported between various predetermined locations, and a sensor cleaning apparatus that is able to detect an output of the sensors and to clean the sensors which become ineffective or inoperative due to a build-up of impurities on the surface of the sensors.

U.S. Pat. No. 5,075,543 discloses an optical sensor in a sheet transport system for detecting a sheet along a paper path having a light beam disposed in an interference relationship with a paper path. An optical fiber provides the means for redirecting the light beam across the paper path.

U.S. Pat. No. 4,793,605 discloses a paper detector comprising a reflection-type photo sensor comprised of a light-emitting element and a light-receiving element for detecting the presence of recording paper inserted in one of the two guide paths. A pivotable detecting lever is pivoted by the recording paper when the recording paper is inserted in the other of the two guide paths, and the pivotal movement of the detecting lever, in turn, displaces a reflecting plate to a position covering the photosensor so that light emitted from the light-emitting is reflected by the reflecting plate to the light-receiving element thereby detecting the presence of paper in the other guide path.

U.S. Pat. No. 4,805,893 discloses an abnormal-paper sensing apparatus in a printing machine which senses the presence of a front folded corner of a sheet of printing paper. An insertion guide plate has a pair of recesses provided in a front end portion thereof so as to extend thereacross at positions where the recesses can face the front corners of the sheet of paper which passes over the recesses. The recess have a triangular cross section with a longer side positioned on the side of the front end of the insertion guide plate and with a shorter side positioned on the side of the rear end of the insertion guide plate. When the sheet of paper hits against front lays provided at the front end of the insertion guide plate and stops, and if the sheet of paper has a folded angle at its front end, the corresponding recess is exposed and reflects the projected light diffusively, so that the sensors do not receive a quantity of reflected light enough to continue paper feeding.

IBM Technical Disclosure, Vol. 22, No. 4, pp. 1585-86, September 1979, discloses a sensor which utilizes a single light beam from a light-emitting diode transmitted to a to phototransistor chip which is twice broken by the same document 16 so that a questionable sheet presence indication is not given by the phototransistor due to light transmittance through pin holes of a document or by virtue of low opacity of the material of document.

Xerox Disclosure Journal, Vol. 10, No. 5, p. 311, September/October 1985, discloses a sensor that utilizes a prism to direct light an emitter to a detector, unless the path is blocked by the presence of the corner of a paper sheet.

In accordance with one aspect of the present invention, there is provided an apparatus for detecting a sheet moving along a path, comprising an emitter adapted to project a light beam, a detector adapted to transmit a signal in response to receiving the light beam and a means for reflecting the light beam between the emitter and the detector. The light beam follows along a light path having a repeating wave form in a plane intersecting the sheet path. The detector transmits a signal indicating the absence of the sheet in response to receiving the light beam and the presence of the sheet in response to the sheet intersecting the light path.

Other aspects and features of the present invention will become apparent as the following description proceeds and upon reference to the drawings, in which.

While the present invention will hereinafter be described in connection with a preferred embodiment thereof, it will be understood that it is not intended to limit the invention to that embodiment. On the contrary, it is intended to cover all alternatives, modifications and equivalents, as may be included within the spirit and scope of the invention as defined by the appended claims.

Figure 11:
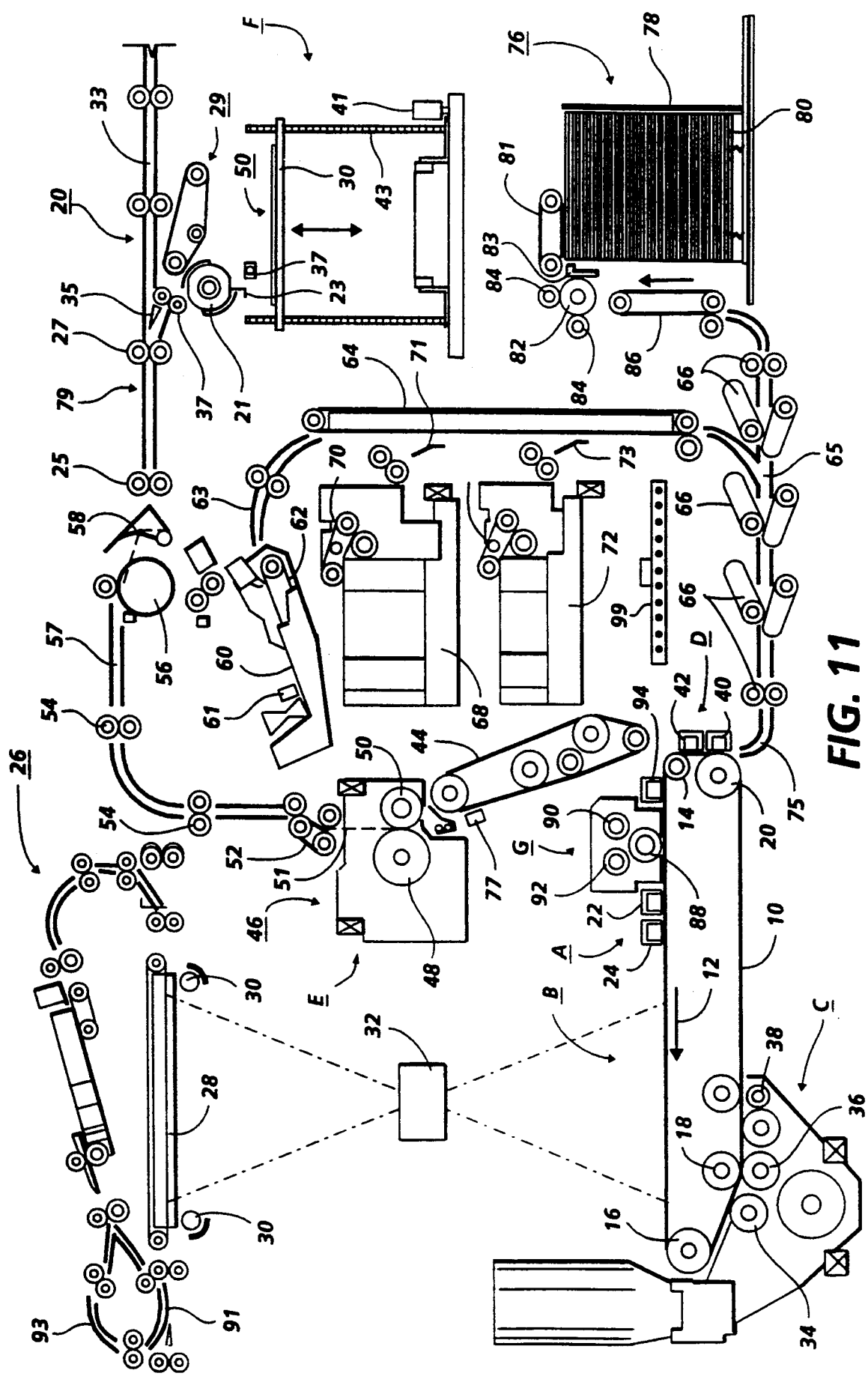
FIG. 11 is a schematic elevational view showing an exemplary document copier or printer having sheet feeding, handling and stacking systems as may incorporate sensors of the present invention therein.

For a general understanding of the features of the present invention, reference is made to the drawings. In the drawings, like reference numerals have been used throughout to identify identical elements. FIG. 11 schematically depicts an electrophotographic copying and/or printing machine incorporating the features of the present invention therein. It will become evident from the following discussion that the sensors of the present invention may be employed in a wide variety of devices and are not specifically limited in application to the particular embodiments depicted herein.

Referring initially to FIG. 11 of the drawings, the electrophotographic printing machine employs a photoconductive belt 10. Preferably, the photoconductive belt is made from a photoconductive material coated on a ground layer, which, in turn, is coated on any anti-curl backing layer. The photoconductive material is made from a transport layer coated on selenium generator layer. The transport layer transports positive charges from the generator layer. The generator layer is coated on an interface layer. The interface layer is coated on a ground layer made from a titanium coated Mylar. The interface layer aids in the transfer of electrons to the ground layer. The ground layer is very thin and allows light to pass therethrough. Other suitable photoconductive materials, ground layers and anti-curl backing layers may also be employed. Belt 10 moves in the direction of arrow 12 to advance successive portions sequentially through the various processing stations disposed about the path of movement thereof. Belt 10 is entrained about stripping roller 14, tensioning roller 16, idler roller 18 and drive roller 20. Stripping roller 14 and idler roller 18 are mounted rotatably so as to rotate with belt 10. Tensioning roller 16 is resiliently urged against belt 10 to maintain belt 10 under the desired tension. Drive roller 20 is rotated by a motor coupled thereto by suitable means such as a belt drive. As roller 20 rotates, it advances belt 10 in the direction of arrow 12.

Initially, a portion of the photoconductive surface passes through charging station A. At charging station A, two corona generating devices, indicated generally by the reference numerals 22 and 24 charge photoconductive belt 10 to a relatively high, substantially uniform potential. Corona generating device 22 places all the required charge on photoconductive belt 10. Corona generating device 24 acts as leveling device and fills in any areas missed by corona generating device 22. Next, the charged portion of the photoconductive surface is advanced through imaging station B.

Next, the charged portion of the photoconductive surface is advanced through imaging station B. At imaging station B, a document handling unit indicated generally by the reference numeral 26 is positioned over platen 28 of the printing machine. Document handling unit 26 sequentially feeds documents from a stack of documents placed by the operator faceup in a normal, forward collated order in the document stacking and holding tray. A document feeder located below the tray forwards the bottom document in the stack to a pair of take-away rollers. The bottom sheet is then fed by the rollers through a document guide to a feed roll pair and belt. The belt advances the document to platen 28. After imaging, the original document is fed from platen 28 by the belt into a guide and feed roll pair. The document then advances into an inverter mechanism and back to the document stack through the feed roll pair. A position gate is provided to divert the document to the inverter or to the feed roll pair. Imaging of a document is achieved by lamps 31 which illuminate the document on a platen 28. Light rays reflected from the document are transmitted through lens 32. Lens 32 focuses light images of the original document onto the charged portion of photoconductive belt 10 to selectively dissipate the charge thereon. Sensors of the present invention at points 91,93 and at other locations in document handling unit 26 can notify the operator of malfunctions, or automatically take corrective actions. This records an electrostatic image on the photoconductive belt which corresponds to the informational areas contained within the original document.

Electronic imaging of page image information could also be facilitated at imaging station B (not shown in FIG. 11), by printing, scanning or copying apparatuses using electrical imaging signals. The printing apparatus can be a digital copier, including an input device such as a raster input scanner (RIS), a printer output device such as a raster output scanner (ROS), or a printer utilizing a printer output device such as a ROS. Such a ROS would be capable of discharging selectively those portions of the charge corresponding to the image portions of the document to be reproduced. In this way, an electrostatic latent image is recorded on the photoconductive surface. An electronic subsystem (ESS) would control the ROS (also not shown in FIG. 11). The ESS would be adapted to receive signals from a computer and transpose these signals into suitable signals for controlling the ROS so as to record an electrostatic latent image corresponding to the document to be reproduced by the printing machine. The ROS may include a laser with a rotating polygon mirror block. The ROS illuminates the charged portion of the photoconductive surface at a rate of about 300 pixels per inch. In this way, a raster electrostatic latent image is recorded on the photoconductive surface which corresponds to the desired information to be printed on the sheet.

After the latent image is recorded on the photoconductive surface, the photoconductive belt 10 rotates the raster electrostatic latent image to development station C. At development station C, three magnetic brush developer rolls indicated generally by the reference numerals 34, 36 and 38 develop the electrostatic latent image. A paddle wheel picks up developer material and delivers it to the developer rolls. When developer material reaches rolls 34 and 36, it is magnetically split between the rolls with half of the developer material being delivered to each roll. Photoconductive belt 10 is partially wrapped around rolls 34 and 36 to form an extended development zone. Developer roll 38 is a clean-up roll. A magnetic roller, positioned after developer roll 38 in the direction of arrow 12, is a carrier granular removal device adapted to remove any carrier granules adhering to belt 10. Thus, rolls 34 and 36 advance developer material into contact with the electrostatic latent image. The latent image attracts toner particles from the carrier granules of the developer material to form a toner powder image on the photoconductive surface of belt 10. Belt 10 then advances the toner powder image to transfer station D.

At transfer station D, a copy sheet is moved into contact with the toner powder image. First, photoconductive belt 10 is exposed to a pretransfer light from a lamp (not shown) to reduce the attraction between photoconductive belt and the toner powder image. Next, a corona generating device 40 charges the copy sheet to the proper magnitude and polarity so that the copy sheet is tacked to photoconductive belt 10 and the toner powder image attracted from photoconductive belt 10 to the copy sheet. Sensors of the present invention at point 75 and at other locations in transfer station D can insure the timing of the image transfer to the copy sheet is properly affected, can notify the operator of malfunctions, or automatically take corrective actions. Sensor 75 and other sensors of the present invention can monitor sheet presence, skew, alignment, trial edge, lead edge and other aspects of sheet handling. After transfer, corona generator 42 charges the copy sheet to the opposite polarity to detack the copy sheet from belt 10. Conveyor 44 advances the copy sheet to fusing station E.

Fusing station E includes a fuser assembly, indicated generally be the reference numeral 46, which permanently affixes the transferred toner powder image to the copy sheet. Preferably, fuser assembly 46 includes a heated fuser roll 48 and pressure roll 50 with the powder image on the copy sheet contacting fuser roll 48. The pressure roll is cammed against the fuser roll to provide the necessary pressure to fix the toner powder image to the copy sheet. The fuser roll is internally heated by a quartz lamp. Release agent, stored in a reservoir, is pumped to a metering roll. A trim blade trims off the excess release agent. The release agent transfer to a donor roll and then to the fuser roll. Sensors of the present invention at points 51, 77 and at other locations in fuser station E can insure fuser timing is properly affected, can notify the operator of malfunctions, or automatically take corrective actions.

After fusing, the copy sheet are fed through a decurler 52. Decurler 52 bends the copy sheets in one direction to a put a known curl in the copy sheet and then bends it in the opposite direction to relax the known curl, so as result in a substantially flat fused sheet.

Forwarding rollers 54 then advance the sheet to duplex turn roll 56. Duplex solenoid gate 58 guides the sheet to the finishing station or to duplex tray 60. At finishing station F, copy sheets are stacked in a compiler tray and attached to one another to form set. The sheets are attached to one another either by a binding device or stapling device. In either case, a plurality of documents are formed in finishing station F. One duplex solenoid gate 58 diverts the sheet into duplex tray 60, duplex tray 60 provides an intermediate or buffer storage for those sheets that have been printed on one side and on which an image will be subsequently printed on the second, opposed side thereof, i.e. the sheets being duplexed. The sheets are stacked in duplex tray 60 face down on top of one another in the order in which they are being reproduced.

In order to complete duplex copying, the simplex sheets in tray 60 are fed, in seriatim, by bottom feeder 62 from tray 60 back to transfer station D via conveyor 64 and rollers 66 for transfer of the toner powder image to the opposed sides of the copy sheets. Inasmuch as successive bottom sheets are fed from duplex tray 60, the proper or clean side of the copy sheet is positioned in contact with belt 10 at transfer station D so that the toner powder image is transferred thereto. Sensors of the present invention at positions 57, 61, 63, 65 and at other locations can cooperatively insure duplex copying or bypass timing is properly affected, can notify the operator of malfunctions, or automatically take corrective actions. The duplex sheet is then fed through the same path as the simplex sheet.

Copy sheets are fed to transfer station D from the secondary tray 66. Secondary tray 66 includes an elevator driven by a bidirectional AC motor. Its controller has the ability to drive the tray up or down. When the tray is in the down position, stacks of copy sheets are loaded thereon or unloaded therefrom. In the up position, successive copy sheets may be fed therefrom by sheet feeder 70. Sheet feeder 70 is a friction retard feeder utilizing a feed belt and take-away rolls to advance successive copy sheets to transport 64 which advances the sheets to roll 66 and then to transfer station D.

Copy sheets may also be fed to transfer station D from auxiliary tray 72. The auxiliary tray 72 includes an elevator driven by a bidirectional motor. Its controller has the ability to drive the tray up or down. When the tray is in the down position, stacks of copy sheets are loaded thereon or unloaded therefrom. In the up position, successive copy sheets are fed therefrom by sheet feeder 74. Sheet feeder 74 is a friction retard feeder utilizing a feed belt and take-away rolls to advance successive copy sheets to transport 64 which advances the sheets to rollers 66 and then to transfer station D. Sensors of the present invention at positions 65, 71, 73 and at other locations can cooperatively insure sheet feeding and timing is properly carried out, can notify the operator of malfunctions, or automatically take corrective actions. A network of optic fibers, wires or other means may be used to centralize information from sensors positioned throughout the machine; a sensor module 99 may centralize light emitting, light sensing, input processing, timing and other sensor functions in a reliable, efficient, cost effective and easily serviced or replaced pullout chassis.

Secondary tray 68 and auxiliary tray 72 are secondary sources of copy sheets. A high capacity feeder, indicated generally by the reference numeral 76, may be a primary source of copy sheets. High capacity feeder 76 includes a tray 78 supported on a elevator 80. The elevator is driven by a bidirectional AC motor to move the tray up or down. In the up position, the copy sheets are advanced from the tray to transfer station D. A fluffer and air knife 83 direct air onto the stack of copy sheets on tray 78 to separate the uppermost sheet from the stack of copy sheets. A vacuum pulls the uppermost sheet against feed belt 81. Feed belt 81 feeds successive uppermost sheets from the stack to a take-away drive roll 82 and idler rollers 84. The drive roll and idler rollers guide the sheet onto transport 86. Transport 86 advances the sheet to roll 66 which, in turn, move the sheet to transfer station D. One skilled in the art will appreciate that a sensor of the present invention may be used at position 93 and in other circumstances in connection with high capacity feeder 76 in determining the absence, presence edge location and/or alignment of a sheet at a selected location.

FIG. 11 also shows a finishing station F, in which sheets may be stacked in stacker 20, which may employ sensors of the present invention. Each sheet stacker 20 includes a rotating disk 21 which includes one or more slots for receiving sheets therein. Rotating disk 21 then rotates to invert the sheet and register the leading edge of the sheet against a registration means or wall 23 which strips the sheet from the rotatable disk 21. Sensors of the present invention at point 79 between stacker feed roller sets 25 and 27 and at other locations in stacker 20 can cooperatively insure disk 21 timing is properly affected so as to stack the sheets, can notify the operator of malfunctions, or automatically take corrective actions. The sheet then drops to the top of the stack of inverted sheets which are supported on a vertically movable by elevator 50. An overhead trail edge assist belt system 29 is located adjacent the rotatable disk 21 and above elevator platform 30 to assist in the inversion of sheets. Elevator platform 30 is moved in a vertical direction by the actuation of a screw drive mechanism 41. The screw drive mechanism includes a separate, vertical, rotatable shaft having a threaded outer surface at each corner of the elevator platform and extending through a threaded aperture therein (four vertical shafts in total). As the two shown vertical shafts 43 and 45 are rotated by a motor, platform 30 is raised or lowered. A stack height sensor 37 is used to control the movement of platform 30 so that the top of the stack remains at substantially the same level. Each stacker 20 also may include a tamping mechanism (not shown) which is capable of offsetting sets of sheets in a direction perpendicular to the process direction, and which may employ one or more sensors of the present invention.

The provision of more than one disk stacker 20 enables sheets to be outputted at higher speeds and in a continuous fashion. A specific requirement of the high speed computer printer market is the ability to provide long run capability with very minimal down time due to system failures, lack of paper supply, or lost time during unload. By providing more than one stacker, the outputting of documents need not be interrupted when one of the stackers becomes full since documents can merely be fed to the other stacker while the full stacker is unloaded. Thus, should one stacker become filled or break down, the outputting of copy sheets is not interrupted. Furthermore, the bypass capability (deflector 35 and bypass transport 33) of each stacker enables stacker 20 to be bypassed so that documents can be fed to other downstream devices such as additional stackers or sheet finishing apparatus, such as, for example, folding or stapling devices.

Before entering sheet stacker 20, the sheets exit through output nips 25 and 27 of an upstream device. The upstream device could be a printer, copier, other disk stacker, or a device for rotating sheets. Sheets may need to be rotated so that they have a certain orientation after being inverted by disk 21. The sheets can enter disk stacker 20 long edge first or short edge first. After entering stacker 20, the sheet is engaged by the nip formed between one or more pairs of disk stacker input rollers. If a bypass signal is provided, bypass deflector gate 35 moves downward to deflect the sheet into bypass transport assembly 33. If no bypass signal is provided, the sheet is directed to disk input rollers 37 which constitute part of the feeding means for feeding sheets to an input position of disk 21.

The movement of the disk 21 can be controller by a variety of means conventional in the art. Preferably, a sensor of the present invention located upstream of disk 21 (at or near position 79) detects the presence of a sheet approaching disk 21. In this manner, a sensor of the present invention at or near position 79 may also be used to inform a control processor when the desired sheet or sheets have cleared bypass deflector gate 35, and may signal the rotation of the disk slot without depending on timing or a constant sheet velocity.

If not assembled in stacker 20, sheets may continue on via bypass transport assembly 33 by deflector gate 35 for processing at subsequent finishing and/or sorter stations not shown in FIG. 11. Sheets may be attached to one another using a binder or stapler to form sets, or otherwise manipulated, sorted and/or processed at such subsequent finishing stations, and which may employ one or more sensors of the present invention.

With continued reference to FIG. 11, after the copy sheet is separated from the photoconductive belt, residual toner particles invariably remain thereon. After transfer, photoconductive belt 10 passes beneath corona generating device 94 which charges the residual toner particles to the proper polarity. Thereafter, a precharge erase lamp (not shown) located inside photoconductive belt 10 discharges the photoconductive belt in preparation for the next successive imaging cycle. Residual particles are removed from the photoconductive surface at cleaning station G. Cleaning station G includes an electrically biased cleaner brush 88 and detoning rolls 90 and 92, i.e. waste and reclaim detoning rolls. The reclaim roll is electrically biased negatively relative to the cleaner roll so as to remove toner particles therefrom. The waste roll is electrically biased positively relative to the reclaim rolls so as to remove paper, debris and wrong sign toner particles. The toner particles on the reclaim roll are scraped off and deposited in a reclaim auger (not shown), where it is transported out of the rear of cleaning station G.

FIGS. 1-10 show various embodiments of the sheet sensor as may be employed with a copier or printer with sheet feeding, handling and stacking system.

Figure 1:
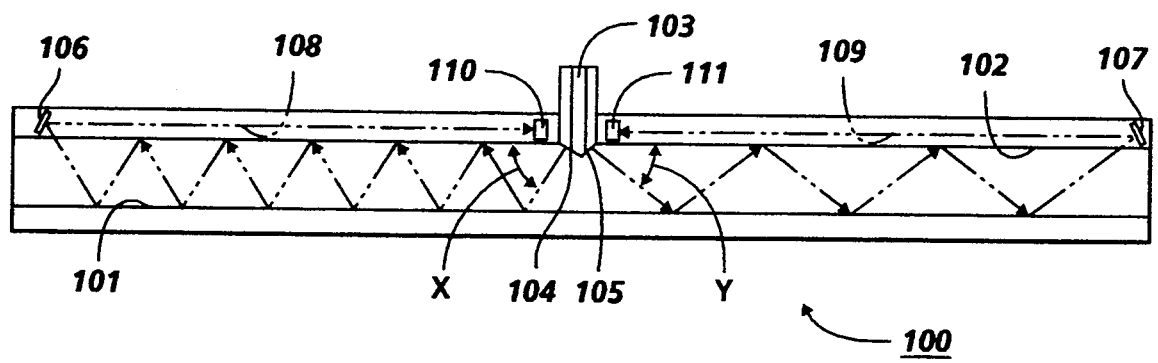
FIG. 1 is a schematic elevational view showing a sheet entry slot and sheet sensor arrangement in accordance with the present invention.

FIG. 1 shows a sensor 100 having a lower reflective surface 101 and an upper reflective surface 102. Emitter 103 provides the light that is bidirectionally directed via lenses 104 and 105 onto lower reflective surface 101. Sheet presence is detected when light emitted from lens 104 is broken by a sheet or object passing between lower reflective surface 101 and an upper reflective surface 102. If no sheet interrupts the path of the beam, it is returned by mirror 106 to receptor 110 adjacent to emitter 104. Likewise, the beam of light emitted from lens 105 is broken by a sheet or object passing between lower reflective surface 101 and an upper reflective surface 102, it is returned by mirror 107 to receptor 111 adjacent to emitter 105. Preferably, in this and other embodiments of the sensor of the present invention, a well focused beam of light is used, so that any light reflected from the sheet will cause the reflector relayed or "zig-zagging" beam of light to miss mirrors 106 and 107, thereby avoiding a false indication. In that no receptors or other operative surfaces are disposed on lower reflective surface 101, there are no recesses or areas for dust and debris to clog or foul in the sensor; rather, the sliding of sheets over lower reflective surface 101 will continuously clean the reflective surface. Likewise, in that receptors 110 and 111 are (preferably) sealed from dust, and are disposed in upper reflective surface 102, sensor clogging or other malfunction is prevented. Preferably, the light emitted from lens 104 is emitted at a different angle (x) towards lower reflective surface 101 than the light emitted from lens 105 (such as an angle y), so as to reduce if not eliminate the possibility of symmetrical holes in the sheet passing through sensor 100 from falsely indicating the lead or trail edge of that sheet. If receptors 110 and 111 do not simultaneously receive light or are not simultaneously blocked from receiving light, a sheet skew condition is indicated.

Figure 2:
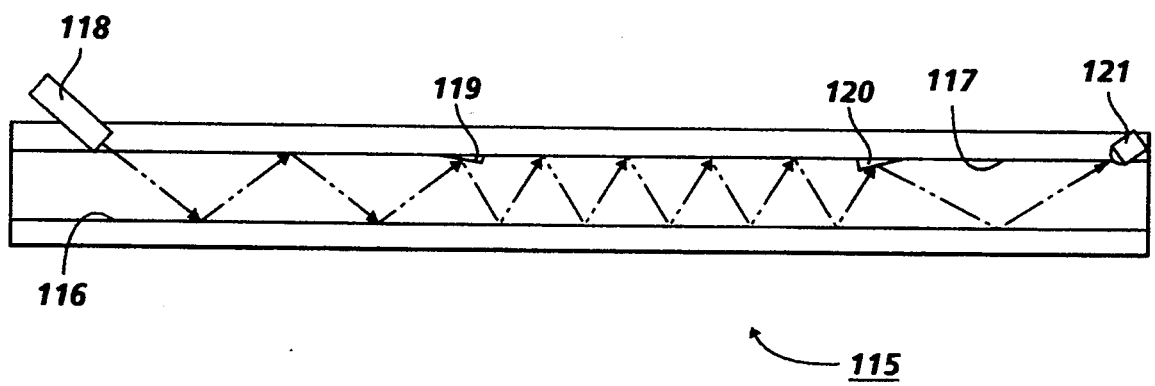
FIG. 2 is a schematic elevational view showing another embodiment of a sheet entry slot and sensor in accordance with the present invention.

FIG. 2 shows a sensor 115 having a lower reflective surface 116 and an upper reflective surface 117. Emitter 118 provides the light that is directed onto lower reflective surface 116; interim reflectors 119 and 120 change the angle of the beam as shown, to reduce if not eliminate the possibility of symmetrical holes in the sheet passing through sensor 115 from falsely indicating the lead or trail edge of that sheet. The beam of light emitted from emitter 118 is broken by a sheet or object passing between lower reflective surface 116 and an upper reflective surface 117. Likewise, in that receptor 121 is sealed from dust and is disposed in upper reflective surface 117 so as to prevent sensor clogging or other malfunction. If no sheet interrupts the path of the beam, it is relayed to receptor 121.

Figure 3:
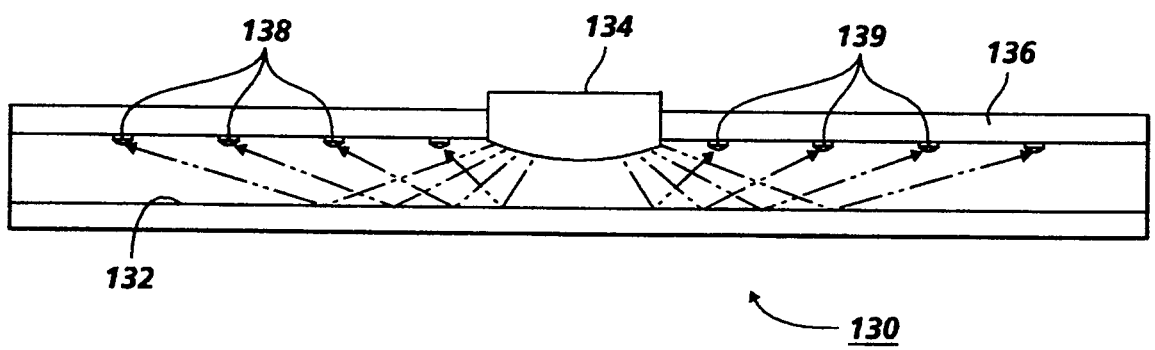
FIG. 3 is a schematic elevational view showing another embodiment of a sheet entry slot and sensor in accordance with the present invention.

FIG. 3 shows a sensor 130 having a lower reflective surface 132 and an upper surface 136 having arrays 138 and 139 of receptors. Emitter 134 provides the light that is multidirectionally directed onto lower reflective surface 132. The beam of light emitted from emitter 134 is broken by a sheet or object passing between lower reflective surface 132 and an upper surface 136. If no sheet interrupts the paths of the beam, it is returned to receptors 138 and 139. The light from emitter 134 is projected at a different angles towards lower reflective surface 132 so as to reduce if not eliminate the possibility of symmetrical holes in the sheet passing through sensor 100 from falsely indicating the lead or trail edge of that sheet. If receptor arrays 138 and 139 do not simultaneously receive light or are not simultaneously blocked from receiving light, a sheet skew condition is indicated.

Figure 4:
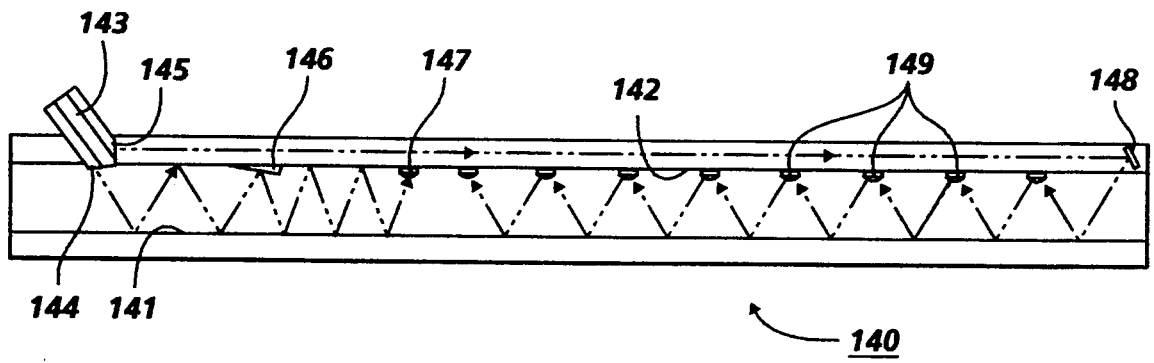
FIG. 4 is a schematic elevational view showing another embodiment of a sheet entry slot and sensor in accordance with the present invention.
Figure 9:
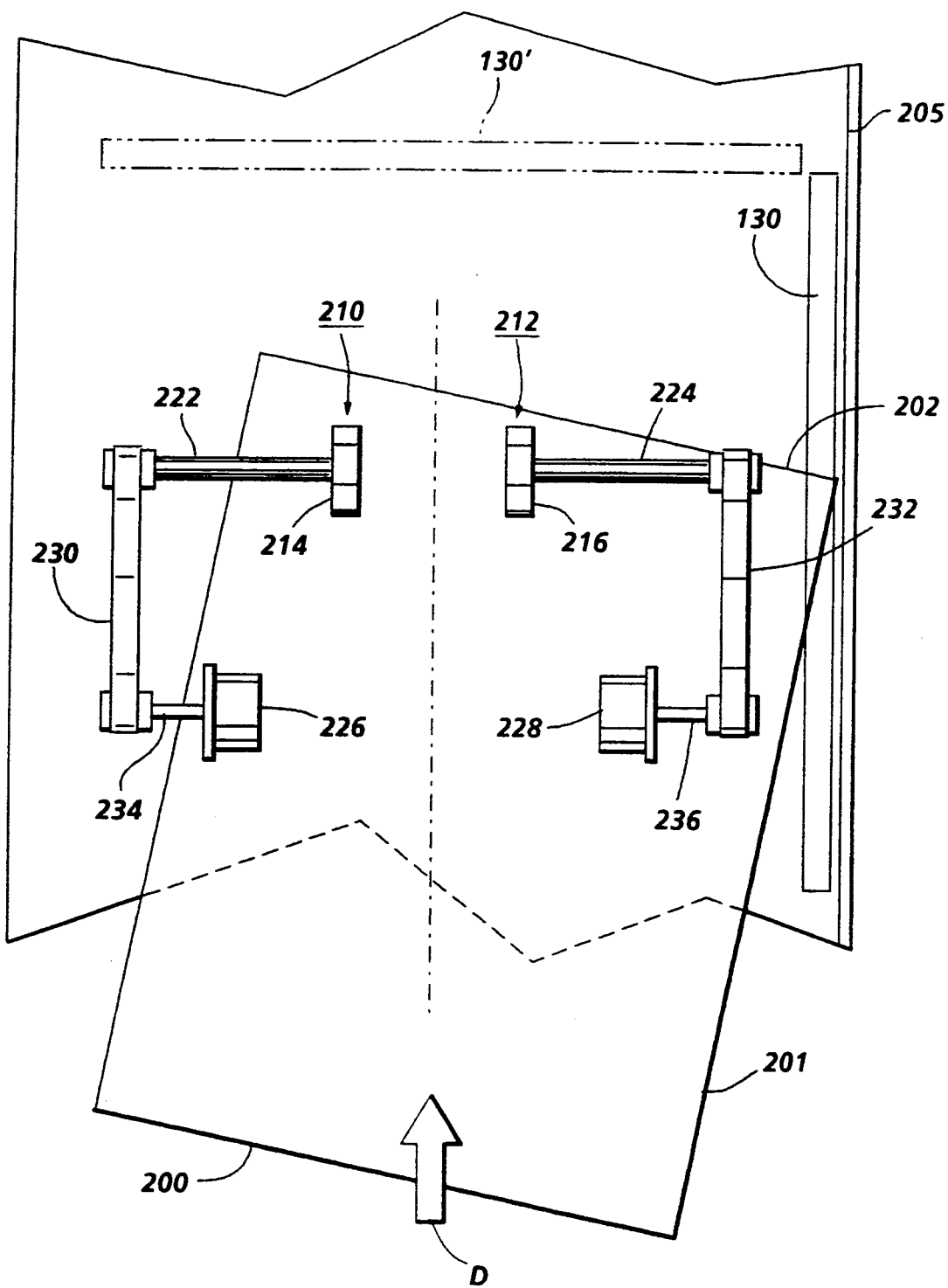
FIG. 9 is an overhead view, partially in section, showing a sheet feeding system utilizing sensors of the present invention.

FIG. 4 shows a sensor 140 having a lower reflective surface 141 and an upper reflective surface 142. Emitter 143 provides the light that is bidirectionally directed via lenses 144 and 145 onto lower reflective surface 141. The beam of light emitted from lens 144 is broken by a sheet or object passing between lower reflective surface 141 and upper surface 142. Interim reflector 146 changes the angle of the beam as shown, to reduce if not eliminate the possibility of symmetrical holes in the sheet passing through sensor 140 from falsely indicating the lead or trail edge of that sheet. If no sheet interrupts the path of the beam, it is returned to receptor 147. The light from lens 145 to mirror 148, and down onto lower reflective surface 141; depending on which receptor 149 are blocked from light by the sheet, the width of the sheet passing through sensor 140 is known. A second sensor 140' (not shown) may be positioned at a right angle to sensor 140, relative to the plane of a passing sheet (see sensors 130 and 130' as shown in FIG. 9). Sensor 140' would be open on the end, so as to permit a sheet to pass lengthwise between surfaces 141' and 142'; light from shared emitter 143 is relayed by lens 145' to mirror 148' and down onto lower reflective surface 141'; depending on which receptor 149' are blocked from light by the sheet, the length of the sheet passing through sensor 140' is known. If receptors 149 and receptor 147 do not simultaneously receive light or are not simultaneously blocked from receiving light, a sheet skew condition is indicated.

Figure 5:
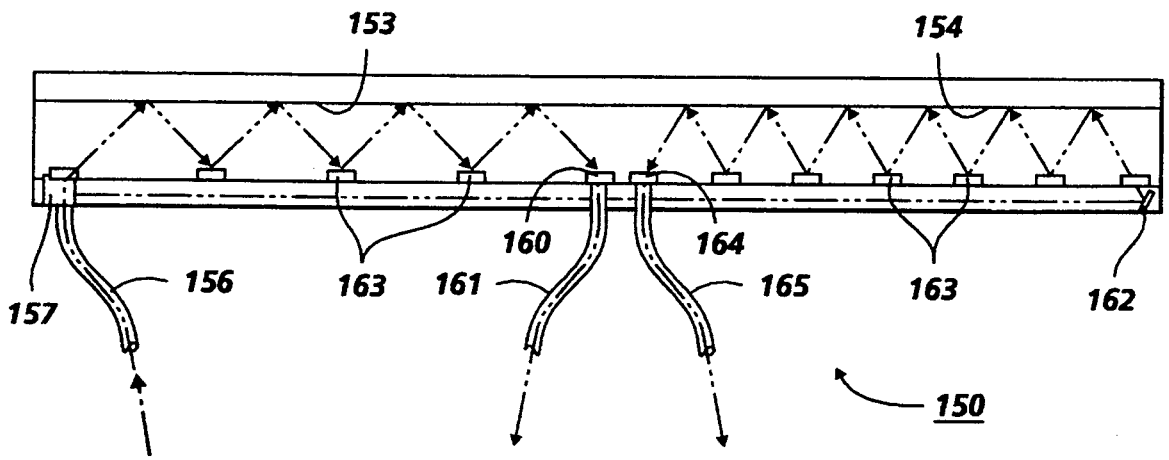
FIG. 5 is a schematic elevational view showing another embodiment of a sheet entry slot and sensor in accordance with the present invention.

FIG. 5 shows a sensor 150 having a lower surface 152 and upper reflective surfaces 153 and 154. Fiber optic member 156 directs light toward upper reflective surface 153 via raised lens 156 and to second raised lens 162, where it is directed towards the upper reflective surface 154. The light in fiber optic member 156 may be supplied from a central location, along with the light to other sensors positioning throughout the copying or printing machine. Illumination from a "power on" or other light source that already serves another purpose in the machine may provide the required light for sensor 150. The necessary light transmitted through fiber optic member 156 may likewise be obtained from an infrared light source, an ultraviolet light source, a laser light source, a white light source, a colored light source, a fiber optic light source and/or even utilize ambient room light. The light sources described above may likewise provide light to the other sensors shown and described in conjunction with FIGS. 1–4 and 6–10 herein. Functional Raised lenses 157 and 162 direct light towards upper reflective surfaces 153 and 154 at differing angles and along differing paths; raised lower reflectors 163 cooperate with upper reflective surfaces 153 and 154 in directing light to raised receptors 160 and 164. Light received by raised receptors 160 and 164 may be relayed to a central location by fiber optic members 161 and 165, respectively, where it is sensed by a photoreceptor, photoresistor, thermistor, thermal sensor or other sensing means. A sheet or object passing between upper reflective surfaces 153 and 154 and lower surface 152 will interrupt the beam of light; if no sheet interrupts the paths of the beam, it is returned to raised receptors 160 and 164. If raised receptors 160 and 164 are not simultaneously blocked from receiving light, a sheet skew condition is indicated. The sliding of sheets over raised reflective surfaces 163, raised lenses 156, 162 and raised receptors 160, 164 provides a continuous cleaning action, preventing dust and debris from interfering with the proper operation of sensor 150. Likewise, false reflections and indications are prevented by the non-raised areas of lower surface 152 that surround the aforementioned raised lenses, reflectors and/or receptors. Further, the uses that can be made of the optic fiber members, emitter lenses, reflectors and/or receptors described in conjunction with FIGS. 6 and 8 may be used in conjunction with other embodiments of the sensor of the present invention. Likewise, the sensors shown and described in conjunction with FIGS. 1–4 and 6–10 herein may be wired and/or optically connected to centralized and/or modularized emitter and receptor assemblies capable of servicing a plurality of sensors throughout the copier or printer machine. Such centralized sensor assemblies with modularized, pull-out chassis could reduce costs while increasing manufacturing, operational and maintenance efficiency. Accordingly, the present invention is intended to embrace all such alternatives, modifications and variations of optic fiber members, lenses, reflectors and/or receptor networks that fall within the spirit and scope of the embodiments described herein.

Figure 6:
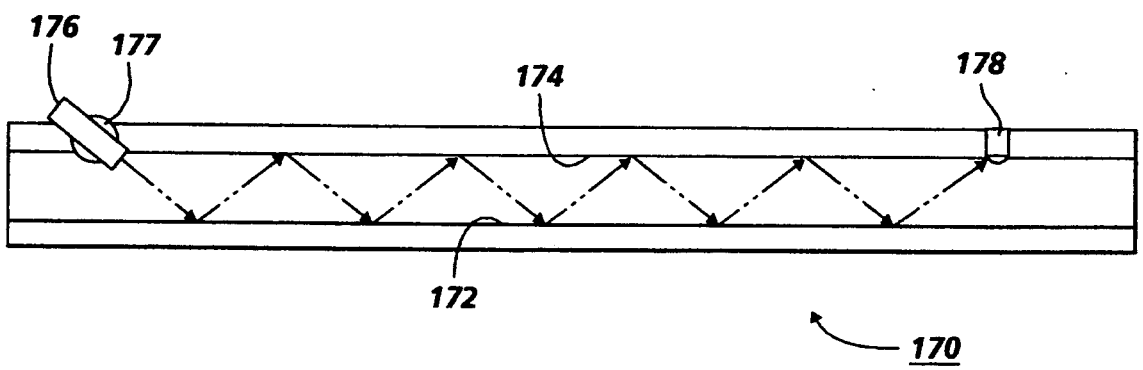
FIG. 6 is a schematic elevational view showing another embodiment of a sheet entry slot and sensor in accordance with the present invention.

FIG. 6 shows a sensor 170 having a lower reflective surface 172 and an upper reflective surface 174. Emitter 176 directs light towards lower reflective surface, so that after being passed back and forth between the upper and lower reflective surfaces it is sensed by receptor 178, provided it is not interrupted by a sheet or object passing between them. Mount 177 may be included on certain embodiments, and may permit the angle of the beam from emitter 176 to be varied, further reducing if not eliminating the possibility that symmetrical holes in a sheet passing through sensor 170 might falsely indicate a lead or trail edge. The distance or gap between lower reflective surface 172 and upper reflective surface 174 may be altered, so as to permit the sensor to detect a stack of sheets, or otherwise permit desired additional sheet clearance. By adjusting emitter 176 in mount 177, or by changing the gap between lower reflective surface 172 and upper reflective surface 174 so as to permit the beam of uninterrupted light to focus on receptor 178, sensor 170 may be employed in a variety of locations in a copier or printer. Light emitted may also be of a nature so that receptor 178 or a secondary receptor positioned in the path of the reflected beam of light, if provided with spectral analysis capability, can determine the color of the sheet. This capability may prevent the accidental use of a colored toner with a sheet of the same color, may automatically adjust toner level(s) and the like to achieve a higher quality print or copy image, or may provide other operational advantage.

Figure 7:
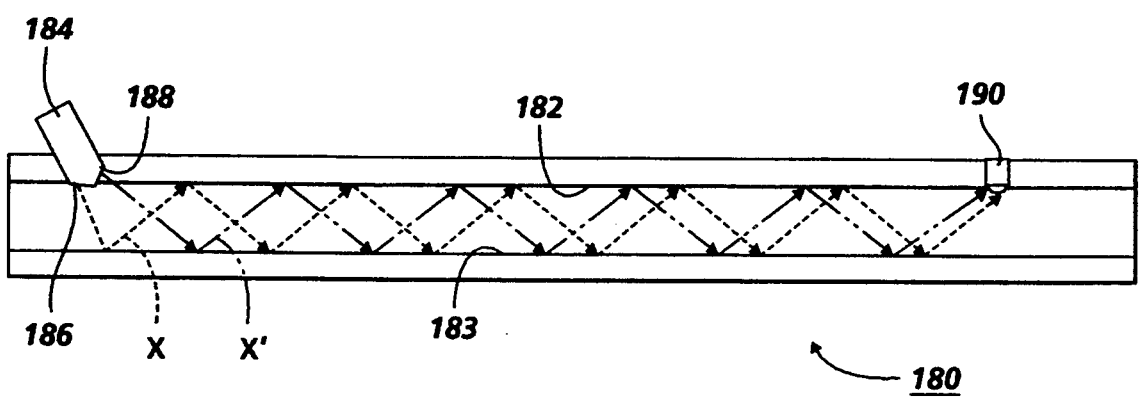
FIG. 7 is a schematic elevational view showing another embodiment of a sheet entry slot and sensor in accordance with the present invention.

FIG. 7 shows a sensor 180 having an upper reflective surface 182 and a lower reflective surface 183. Emitter 184 directs beams X and X' of light from lenses 186 and 188; the beams may be identical or of differing spectral characteristics to permit receptor 190 to differentiate between them. Light is directed towards lower reflective surface 184, and after being transmitted back and forth between the upper and lower reflective surfaces (except as it is interrupted by a sheet resting or passing between them) is sensed by receptor 190.

Figure 8:
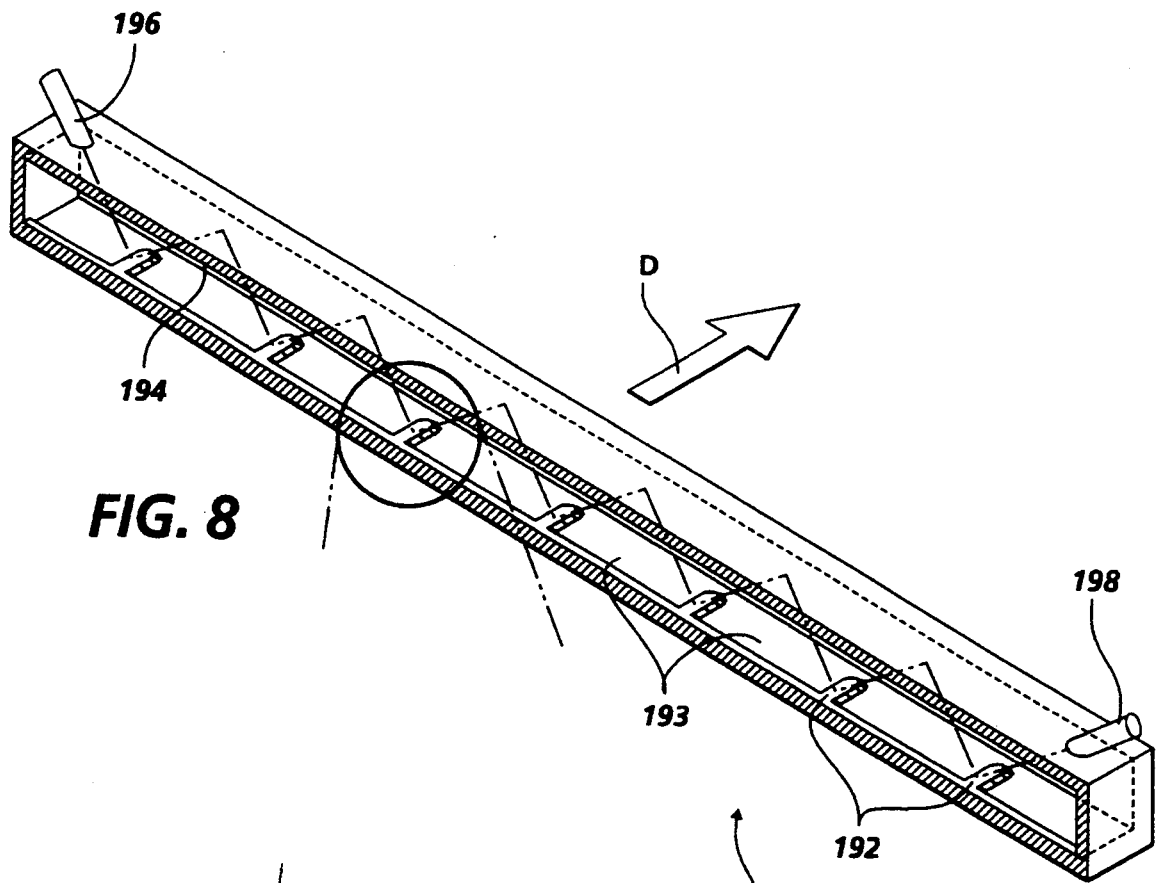
FIG. 8 is a perspective view showing a sheet sensor of the present invention.
Figure 8A:
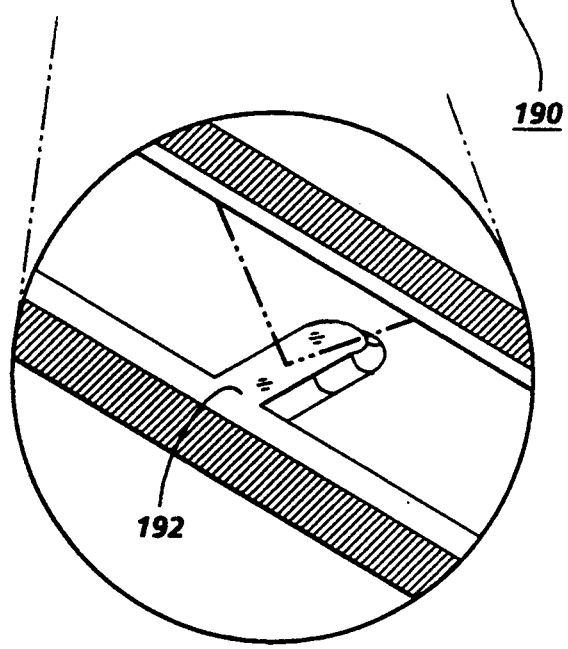
FIG. 8A is an enlarged view showing an area of the sheet sensor shown in FIG. 8.

FIG. 8 is a perspective view show another embodiment of the present invention. Sensor 190 includes raised reflective surfaces 192 between recessed areas 193 on the lower surface of sensor 190. Emitter 196 directs parallel beams of light towards the lower reflective surfaces 192, and after being passed back and forth between them and upper reflective surface 194 (except as interrupted by a sheet passing between them) is sensed by receptor 198. The sliding of sheets in direction D over raised reflective surfaces 192 (also shown enlarged in FIG. 8A) provides a continuous cleaning action; dust and debris is trapped or directed away from the sensor by recesses 193. False reflections are also prevented by recesses 193, and by the narrow width of reflective surfaces 192, which only permit properly focused light to reach receptor 198.

FIG. 9 shows a sheet registration system which utilizes sensor(s) of the present invention to provide an active registration system which sense document position and operates to correct that positioning if necessary. A sheet deskewing arrangement may be provided with a sensor 130 having open ends (and/or a second sensor 130') as described in conjunction with FIG. 3, or other suitable multidetector sensor described herein. Each sensor may be arranged along a sheet path, operably coupled with selectably controllable drive motors each driving a driving nip in a nip roll pair, to correct skew sensed by the sensors. The sensors detect when a lead and/or side edge of a sheet passes thereby; a difference in the timed sensing of individual receptors (as described in conjunction with FIGS. 1–8 above) will indicate sheet skew, and the two motors are driven in accordance with the difference to accelerate or decelerate a side portion of the sheet, thereby rotating the sheet to bring the sheet into proper alignment and registration. Edge stop 205, adjacent to sensor 130 (and/or receptor arrays 138 and 139 as shown in FIG. 3) can monitor and prevent lateral shift of sheet 200, and otherwise insure uniform positioning and feeding of each sheet for subsequent operations in the copier or printer.

FIG. 9 shows a sheet registration, alignment and/or deskewing system that utilizes one or more sensors of the present invention. Sheet 200 is fed by drive rolls (not shown) in direction D toward the registration roll sets 210 and 212, which has been initialized at the approximate centerline of the paper path. Leading edge 202 of sheet 200 initially contacts one side of the registration rolls, in this case, roll pair 214 and 216, which rolls are initially in a stopped position. Stepper motor 226 drives belt 230 on roller axles 222 and 234; likewise, stepper motor 228 drives belt 232 on roller axles 224 and 236. Cooperatively, these stepper motors manipulate the positioning of sheet 200 according to the information provided by sensor(s) 130 and/or 130'. A controller (nor shown) counts the steps taken by the stepper motor; an appropriate edge 201 and/or 202 is sensed by the sensors 130 and/or 130'. In this manner, sheet 200 continues to be driven forward by drive rolls in the direction of arrow D until a side edge 201 fully engages sensor 130, and/or until lead edge of sheet 202 fully engages sensor 130'; according to the information provided by the sensor as to the skew of the sheet, sheet 200 is rotated until sheet leading edge 202 is aligned in both registration roll pairs 210 and 212. Once the sheet 200 is in the proper registration/alignment position, it continues to be driven in the direction of arrow D by unison rotation of rollers 214 and 215. Depending on which individual receptor(s) in arrays 138 and 139 are blocked from light by sheet 200 (see FIG. 3), sensors 130 and or 130' can determine whether the sheet is laterally shifted and/or skewed. Preferably, stepper motors 226 and 228 manipulate side edge 202 to engage sensor 130; edge stop 205 may assist in insuring that side edge 202 is uniformly positioned for subsequent operations in the copier or printer. Registration roll sets 210 and 212 then prepare to accept the next sheet.

The path of sheet 200 in FIG. 9 may be provided with one or more sensors 130 and 130' as shown and described in accordance with FIG. 3, or a combination of other sheet sensors in place of sensors 130 and 130' such as those shown and described above in accordance with FIGS. 1-2 and 4-10. Sensors may be spaced apart on a line which is substantially perpendicular to the path of travel of sheet 200, at right angles, or otherwise according to the desired function, as well as to accommodate the available space in the copier or printer.

Figure 10:
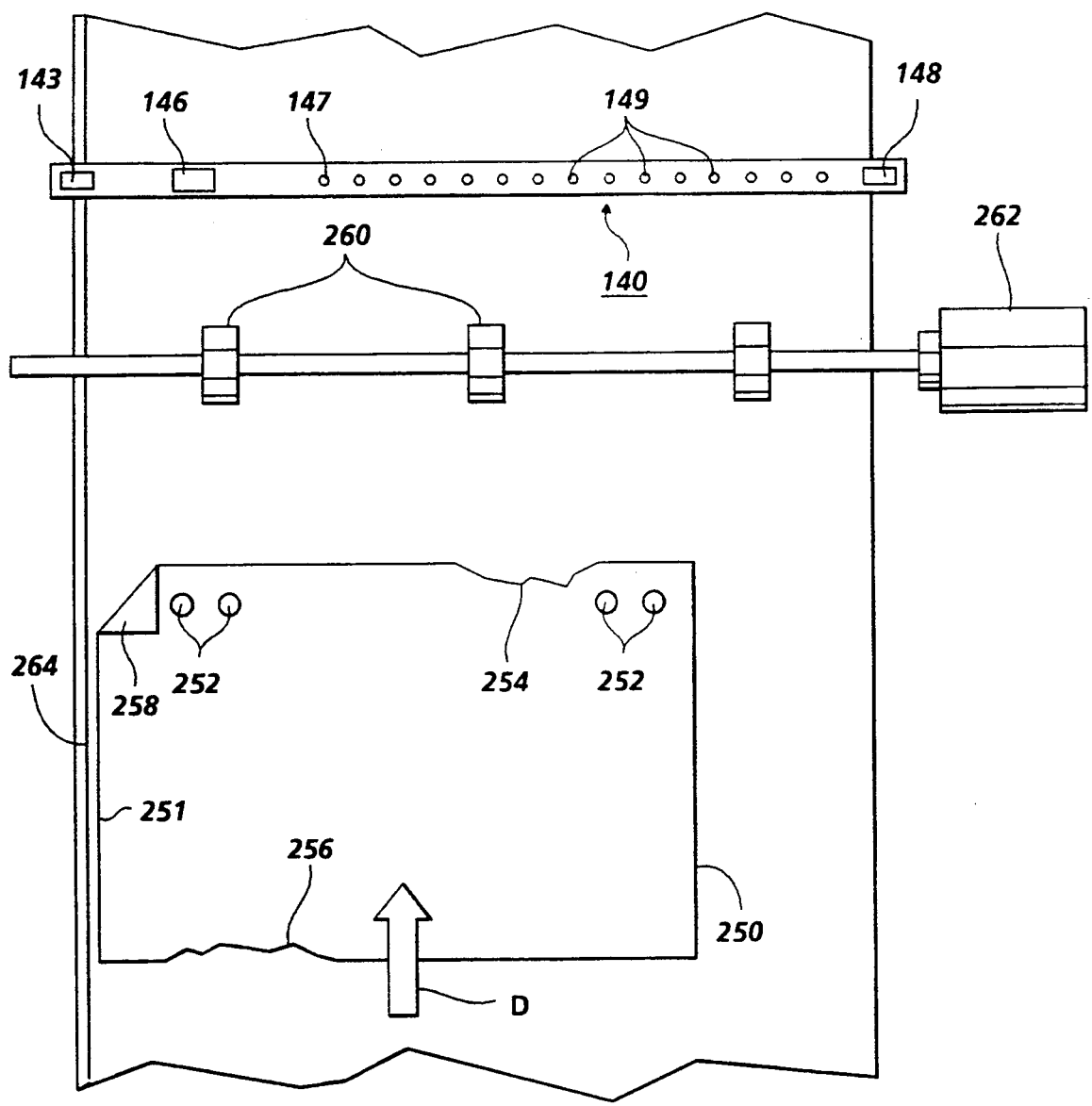
FIG. 10 is an overhead view, partially in section, showing a sheet feeding system utilizing sensors of the present invention.

FIG. 10 shows a schematic representation of another sheet feed system that may utilize one or more sensors of the present invention. Such an arrangement incorporating the sensor(s) of the present invention finds advantageous use in any application where the alignment and/or presence of discrete sheets of material must be fed, registered or otherwise moved through a copier or printer. Uses include, for example, a primary, auxiliary or high volume copy sheet feed or stack setup, a recirculating document handler, and numerous others. Sheet 250, with predrilled holes 252, torn lead edge 254, torn trail edge 256 and folded corner 258 is shown being moved in FIG. 10. Sheet 250 is fed into feed rollers 260 powered by motor 262 in direction D; despite the irregular edges and unusual hole configuration of sheet 250, sensor 140 is able to correctly sense (depending on which receptors of receptor array 149 are blocked from light) the width and presence of sheet 250; likewise, due to the changes the angle of the light beam (see FIG. 4), the lead an/or trail edge of sheet 250 is properly indicated by sensor 140. Sheet 250 is fed so that edge 251 is adjacent to edge stop 264. As sheet 250 interrupts the path of the beam, if receptor array 149 and receptor 147 do not simultaneously receive light or are not simultaneously blocked from receiving light, a sheet skew condition is indicated.

While the invention has been described in conjunction with a specific embodiment thereof, it is evident that many alternatives, modifications, and variations will be apparent to those skilled in the art. Accordingly, it is intended to embrace all such alternatives, modifications and variations that fall within the spirit and scope of the appended claims.

We claim:

1. An apparatus for detecting a sheet moving along a path, comprising:
    an emitter adapted to project a light beam;
    a detector adapted to transmit a signal in response to receiving the light beam; and
    means for reflecting the light beam between said emitter and said detector along a light path having a repeating wave form in a plane intersecting the sheet path, said detector transmitting a signal indicating the absence of the sheet in response to receiving the light beam and presence of the sheet in response to the sheet intersecting the light path.

2. The apparatus of claim 1, wherein said reflecting means comprises a plurality of substantially planar surfaces adapted to cooperatively focus the light beam along the light path from said emitter to said detector.

3. The apparatus of claim 2, wherein said plurality of planar surfaces comprise planar surfaces positioned to contact the sheet moving along the sheet path.

4. The apparatus of claim 2, wherein said plurality of planar surfaces comprise at least two substantially planar surfaces mounted opposed from one another defining a slot therebetween through which the sheet advances.

5. The apparatus of claim 1, wherein said emitter is selected from the group consisting of an infra red light source, an ultraviolet light source, a laser light source, and a white light source.

6. The apparatus of claim 1, wherein said reflecting means is a mirror.

7. The apparatus of claim 1, further comprising a processor receiving the signal from said detector to sense an edge of the sheet.

8. The apparatus of claim 1, further comprising a processor receiving the signal from said detector and in response thereto, being adapted to discriminate between an aperture in the sheet and the absence of the sheet.

9. The apparatus of claim 1, further comprising:
    a second detector further adapted to transmit a second signal in response to receiving a second light beam; and
    a processor capable of accepting input from said first mentioned detector and said second detector so as to detect a length of at least one edge of said sheet.

10. The apparatus of claim 1, wherein said detector is selected from the group consisting of a photoreceptor, a photoresistor, a thermistor and a thermal sensor.

11. The apparatus of claim 1, further comprising a second reflector means, wherein said second reflector means is positioned so as to alter an angle of incidence of the light being reflected to said detector.

12. The apparatus of claim 1, wherein said emitter projects the light beam along a plurality of light paths.

13. The apparatus of claim 1, further comprising a second light detector.

14. The apparatus of claim 1, wherein said detector detects a color of the sheet.

* * * * *